(12) United States Patent
Shaw

(10) Patent No.: US 9,266,923 B2
(45) Date of Patent: Feb. 23, 2016

(54) COMPOSITIONS AND METHODS FOR TREATMENT OF THROMBOSIS AND FOR PROLONGING SURVIVAL OF STORED PLATELETS

(76) Inventor: Gray D. Shaw, Milton, MA (US)

(*) Notice: Subject to any disclaimer, the term of this patent is extended or adjusted under 35 U.S.C. 154(b) by 888 days.

(21) Appl. No.: 13/168,048

(22) Filed: Jun. 24, 2011

(65) Prior Publication Data
US 2012/0165258 A1    Jun. 28, 2012

Related U.S. Application Data

(60) Provisional application No. 61/398,342, filed on Jun. 24, 2010.

(51) Int. Cl.
*C07K 7/08*    (2006.01)
*A61K 31/4152*    (2006.01)
*A61K 38/19*    (2006.01)
*A61K 45/06*    (2006.01)
*A61K 47/48*    (2006.01)

(52) U.S. Cl.
CPC ............... *C07K 7/08* (2013.01); *A61K 31/4152* (2013.01); *A61K 38/196* (2013.01); *A61K 45/06* (2013.01); *A61K 47/48215* (2013.01)

(58) Field of Classification Search
CPC ........................................................ C07K 7/08
USPC ................... 530/326, 381; 514/21.5, 13.8
IPC ............ C07K 7/00, 14/745; A61K 38/03, 38/10
See application file for complete search history.

(56) References Cited

U.S. PATENT DOCUMENTS 5,614,549 A * 3/1997 Greenwald et al. ........... 514/449
6,566,506 B2 * 5/2003 Greenwald et al. ........ 530/391.1
2005/0136056 A1 6/2005 Kageyama

FOREIGN PATENT DOCUMENTS

WO    2004011030    5/2004
WO    2012013709    2/2012

OTHER PUBLICATIONS

Benard (Biochemistry 47(16), 4674-4682, 2008).*
McEwan (Blood 114(23) 4883-4885, 2009).*
Vanhoorelbeke et al., Current Pharmaceutical Design, 13:2684-2697 (2007).
Rumjantseva et al., Nature Medicine, 15:1273-1281 (2009).
Lopez, Blood, 114:4757-58 (2008).
Simon et al., J. Exp. Med., 192:193-204 (2000).
Ehlers et al., J. Exp. Med., 198:1077-88 (2003).
Hoffmeister et al., Cell, 112:87-97 (2003).
Benard et al., Biochemistry, 47:4674-4682 2008).
McEwan et al., Blood, 114:4883-85 (2009).

* cited by examiner

*Primary Examiner* — David Lukton

(57) ABSTRACT

Provided herein are methods and compositions, including pharmaceutical compositions, for treating thrombosis, vascular inflammation, and thrombocytopenia. The methods and compositions of the present invention are also useful for extending the useful storage shelf life of platelets.

20 Claims, 4 Drawing Sheets

COMPOSITIONS AND METHODS FOR TREATMENT OF THROMBOSIS AND FOR PROLONGING SURVIVAL OF STORED PLATELETS

RELATED APPLICATIONS

This application claims priority from provisional patent application Ser. No. 61/398,342, filed on Jun. 24, 2010.

TECHNICAL FIELD

This application pertains to methods and compositions, including pharmaceutical compositions, for the treatment of thrombosis, vascular inflammation and thrombocytopenia. This application further pertains to methods and compositions that are useful for improving the capacity to store platelets. In particular, this invention provides methods and materials prevent the rapid clearance of transfused platelets after cold storage or refrigeration, such that the useful life of cold stored platelets can be extended beyond 48 hours.

BACKGROUND

The worldwide demand for platelets is increasing, in large part due to their prophylactic use to prevent bleeding in thrombocytopenic cancer patients. The success of new therapies, especially for patients with blood cell cancers, is helping to drive up the number of annual cases of therapy-related thrombocytopenia. Typically patients receive platelet transfusions when their platelet count falls below a "trigger" threshold level and thus the frequency of transfusions in thrombocytopenic patients, in part, depends on the circulating lifespan of the transfused platelets. Interestingly, it has been recently reported that the lifespan of circulating platelets largely depends on the amount of exposed penultimate residues contained in platelet surface glycan structures. On nascent platelets, these residues are normally capped and "masked" by sialic acid. The terminal sialic acid residues on glycan chains can be removed by sialidase enzymes present in blood. Loss of sialic acid on the platelet surface glycans, in turn, then leads to a more rapid clearance of platelets by hepatocytes and macrophages. See Sørenson et al., *Blood*, 114: 1645-1654 (2009). Accordingly, an agent that could prevent this more rapid in vivo platelet clearance and sustain circulating platelet levels for longer periods of time, should provide a more efficient prophylactic therapy for thrombocytopenic patients.

Storage of platelets for transfusions has long been a difficult issue. According to the Food and Drug Administration's Blood Products Advisory Committee statement, issued Mar. 15, 2002, entitled "Review of Data Supporting Extension of Dating Period for Platelets": "Bacterial contamination of platelet products continues to be a problem with a contamination rate estimated at 1/2000 units. Storage of platelets at room temperature for up to 5 days allows for proliferation of bacteria in platelet units, and "older" platelets have been associated with increased incidence of septic transfusion reactions. Various approaches are being developed that would either screen or chemically decontaminate platelet units prior to transfusion. If such methods are shown to decrease bacterial contamination of platelet products, storage of platelets out to 7 days may become practical."

Attempts have been made to reduce the incidence of contamination and extend the storage life of platelets by refrigeration or cold storage. See, Snyder and Rinder, N. E. J. Med. 348:2032-2033 (2003). However, platelets, unlike other transplantable tissues or cell types, do not tolerate refrigeration and disappear rapidly from the circulation if subjected to chilling before transplantation or transfusion. See Rumjantseva et al., Nature Medicine, 15:1273-80 (2009).

Andrews and Berndt, Current Biology, 13:R282-84 (2003) suggest that during chilling of platelets GPIbα could be modified in such a way that cold platelet storage may be feasible by maintaining hemostatic activity and preventing accelerated clearance. However, attempts to inhibit the rapid clearance of long-term stored, chilled platelets have thus far achieved very limited success. For example, Wandall et al., Blood, 111: 324956 (2008) report the inability to prevent rapid clearance through galactosylation. Hoffmeister et al., US Patent Application 2008/0138791, report some success in reducing clearance and thereby prolonging the survival of platelets through glycan modification of GPIbα molecules.

The useful life of platelets stored at room temperature remains limited because of the risk of contamination and loss of function. The current inability to chill platelets for longer-term storage, thereby allowing the "stockpiling" of platelets with preserved function, results in chronic shortages of platelets for clinical transfusions and adds to the overall costs of clinical platelet transfusions.

GPIb-IX-V is a multifunctional hetero-complex of four distinct glycoprotein chains, abundantly found on the surface of platelets. The GPIbα chain is one of the subunits of GPIb-IX-V and its N-terminal domain is capable of interacting with several proteins that are either circulating in or exposed to the bloodstream. These proteins include von Willebrand Factor (VWF), thrombin, Factor XI, Factor XII, kininogen, thrombospondin 1 (TSP-1), integrin Mac-1 (CD11b/CD18, $\alpha_M\beta_2$ or CR3), P-selectin, as well as Ashwell-Morell receptors. Because of this range of interactions, GPIbα has a broad role in platelet function with regard to thrombosis, hemostasis and inflammation. Specific binding events mediated by GPIbα can be separated and vary in importance to hemostatic function. For example the importance of regulated binding to VWF is demonstrated by the finding that a single amino acid substitution in the N-terminal domain of GPIbα can cause gain-of-function phenotypes resulting in human platelet-type von Willebrand disease.

Recent experimental evidence suggests that when platelets are collected and cooled by refrigeration during storage prior to transfusion, the GPIbα glycoprotein chain plays a key role in mediating the subsequent rapid clearance of those transfused platelets from the circulation of the recipient. This rapid clearance has been reported to involve surface clustering of the glycans and protein components of GPIbα on stored platelets, which are observed to form interactions with the recipient's Mac-1 and the Ashwell-Morell asialoglycoprotein receptors. See Rumjantseva et al., Nature Medicine, 15:1273-80 (2009).

Given the role that GPIbα plays with regard to multiple platelet functions, it has been previously contemplated that a specific antagonist to one or more of the GPIbα interaction domains might have therapeutic value in treating cases of undesired thrombosis, inflammation, thrombocytopenia, and rapid platelet clearance. However, experimental attempts using proteins, including antibodies and antibody derived fragments, to block the GPIbα interaction domains have typically resulted in undesired thrombocytopenia. Thus, there exists the need in the art for a therapeutic agent or drug that will serve as a specific GPIbα binding domain antagonist, without causing undesired thrombocytopenia. Moreover, a drug that selectively inhibits certain GPIbα binding functions, yet preserves the capacity of the platelet to maintain its other hemostatic functions, would have substantial therapeutic utility in a variety of vascular disease settings.

The discovery, using a phage display screening approach, of a ten amino acid cyclic peptide termed OS-1, capable of binding to the N-terminal domain of GPIbα was recently reported by Benard et al., Biochemistry, 47:4674-82 (2008). The ability of OS-1 to block VWF-mediated platelet aggregation in vitro, was reported with this peptide. Two other peptides, designated as PS-4 and OS-2, were also shown to competitively inhibit the interaction between VWF-A1-domain and GPIbα. However, no in vivo data was provided in this study and inhibition of Mac-1 binding to GPIbα was not demonstrated. Indeed, simultaneous inhibition of both VWF and Mac-1 binding is unexpected for small peptides. In fact, using small peptides as inhibitors, it has been reported that the binding sites for VWF and Mac-1 on GPIbα are inhibited independently and therefore distinct binding sites. Munday et al., Blood (ASH Annual Meeting Abstracts) 114:472 (2009) and oral presentation Dec. 7, 2009. The N-linked glycans present on GPIbα having exposed βGlcNAc and/or galactose residues represent an entirely separate point of interaction between either GPIbα and Mac-1 or GPIbα and the asialoglycoprotein (Ashwell-Morell) receptors. Given its small size, it is unlikely the OS-1 peptide is able to create a steric interference of this interaction.

McEwan et al., Blood 114:4883-85 (2009) describes the non-covalent interaction of OS-1 peptide with GPIbα and demonstrates that the GPIbα-OS-1 complex structure overlaps with the structure of the GPIbα-VWF A1 domain complex. This indicates that the OS-1 peptide directly interferes with binding of VWF to GPIbα. In commenting on the findings of McEwan, Lopez and Munday, Blood 114:4757-58 (2009) hypothesized that the OS-1 peptide occupies the site where VWF would interact with GPIbα and effects a conformational change in GPIbα that prevents formation of the GPIbα-VWF complex.

There remains a need for improved methods and materials useful for extending the useful storage life of platelets. Such methods should reduce the contamination of platelets, for example, by reducing bacterial and viral growth, yet substantially preserve the platelet's hemostatic function and in vivo half-life after transfusion. There is a further need for methods and materials for the treatment of thrombosis, vascular inflammation, thrombocytopenia, and other platelet-related disorders.

BRIEF SUMMARY OF THE INVENTION

The present invention describes the creation of novel cyclic peptides, extending the structure of OS-1 and enabling the conjugation to polymers such as polyethylene glycol, while retaining the binding activity to platelet GPIbα. These novel conjugated cyclic peptides (termed CCPs) demonstrate an enhanced activity for blocking specific interactions mediated by GPIbα on the platelet surface. Moreover, these CCPs have suitable biological and pharmacokinetic properties for use as therapeutic agents in humans. Methods are further described for using CCPs to treat humans with thrombotic or inflammatory disorders. In addition, methods are also described for using CCPs to prevent the rapid clearance of cold stored platelets following transfusion.

BRIEF DESCRIPTION OF THE SEQUENCES

Figure 1:
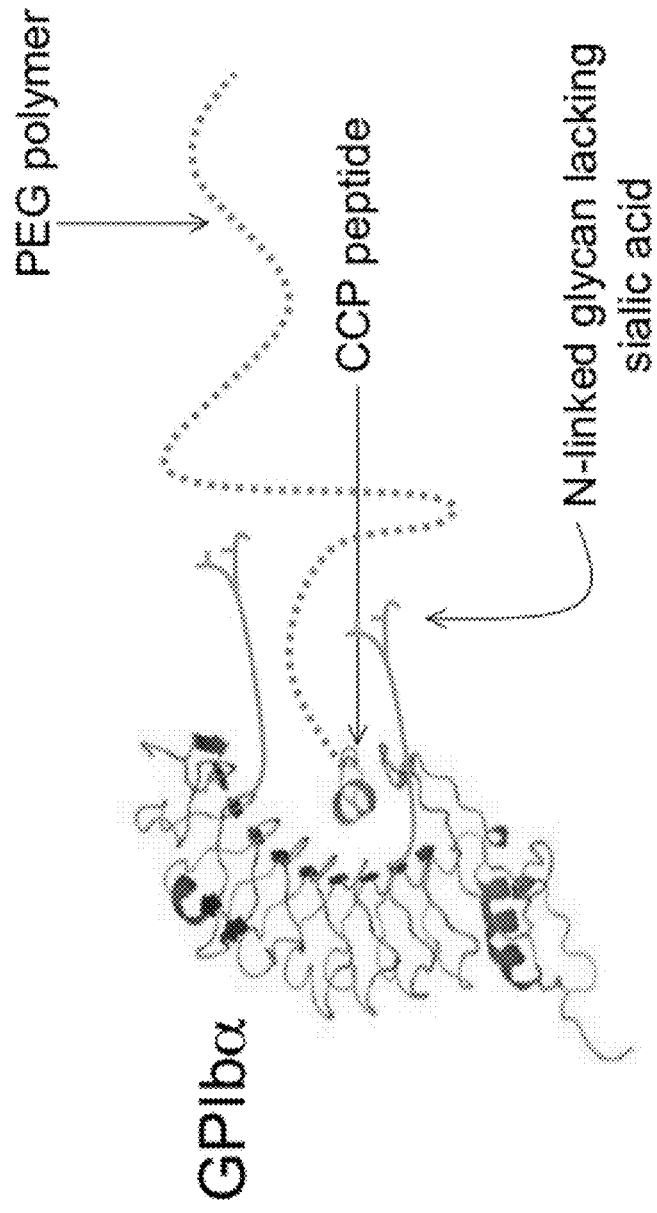
FIG. 1 Schematic depiction of a CCP binding to GPIbα. The presence of the PEG polymer chains can inhibit the binding of N-linked glycans by lectin-like receptors.
Figure 2:
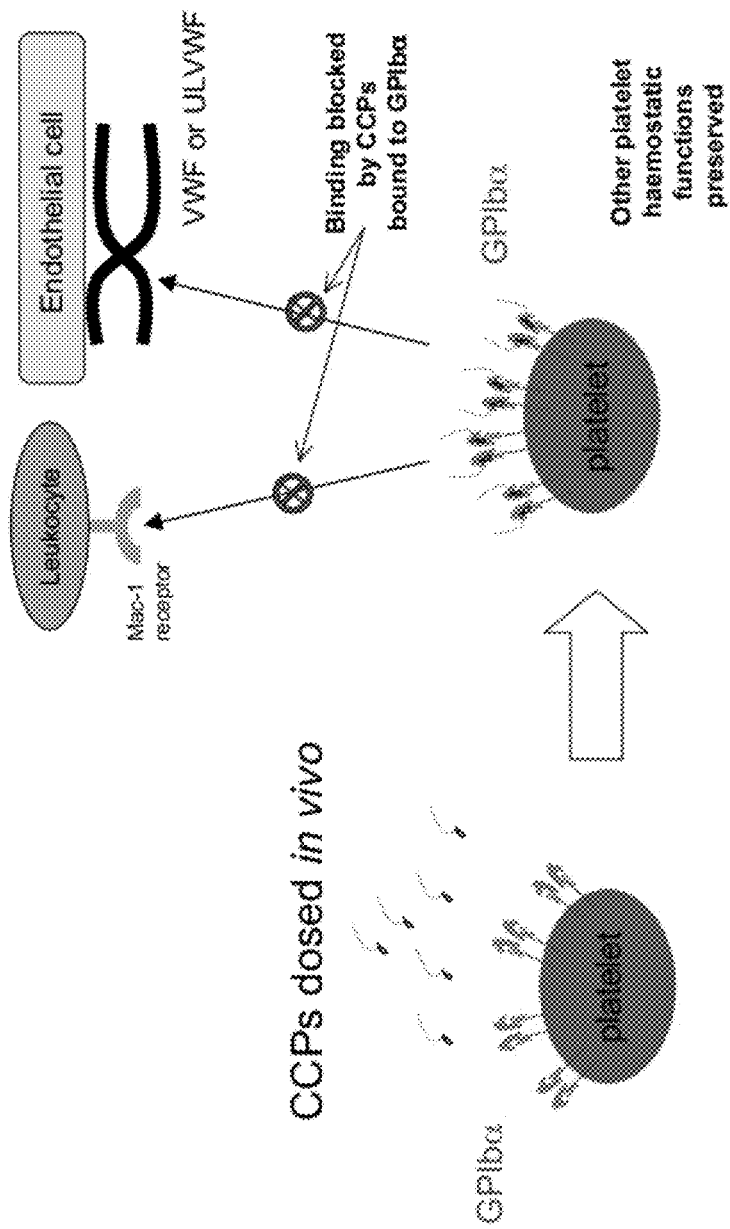
FIG. 2 Schematic depiction of the in vivo use of CCPs to prevent thrombosis and/or inflammation. After administration, CCPs bind in a non-covalent fashion to GPIbα on the surface of circulating platelets and then prevent binding to Mac-1 and VWF or ULVWF.
Figure 3:
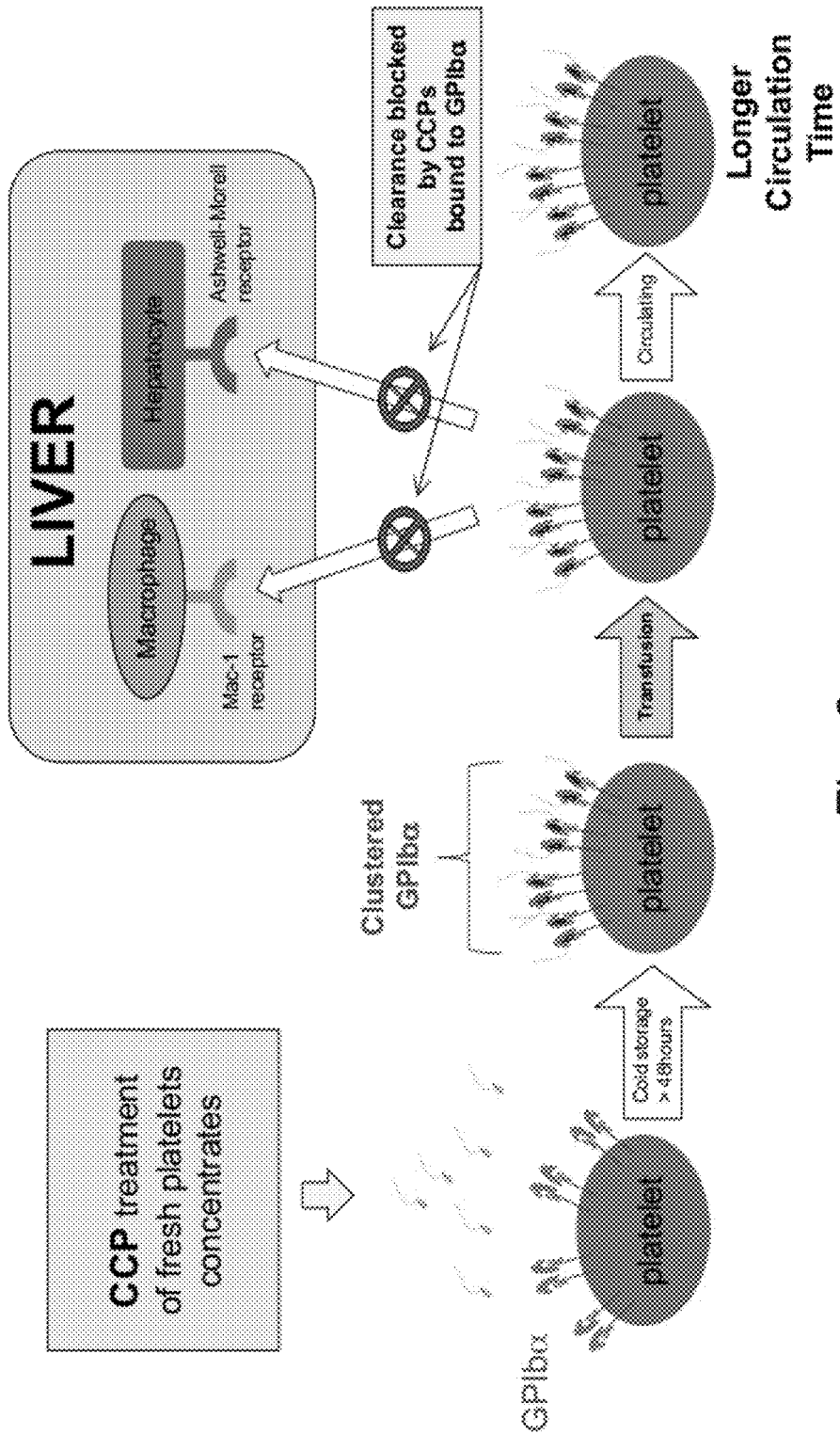
FIG. 3 Schematic depiction of the ex vivo use of CCPs to enable cold storage of platelets for greater than 48 hours. CCPs bind in a non-covalent fashion to GPIbα on the surface of isolated platelets and then, following cold storage and transfusion, block specific platelet binding functions such as the binding to the lectin-like Mac-1 integrin receptors on macrophages (Kupffer cells) and/or the Ashwell-Morrel asialoglycoprotein receptors on hepatocytes. This prevents rapid platelet clearance while preserving useful platelet functions.
Figure 4:
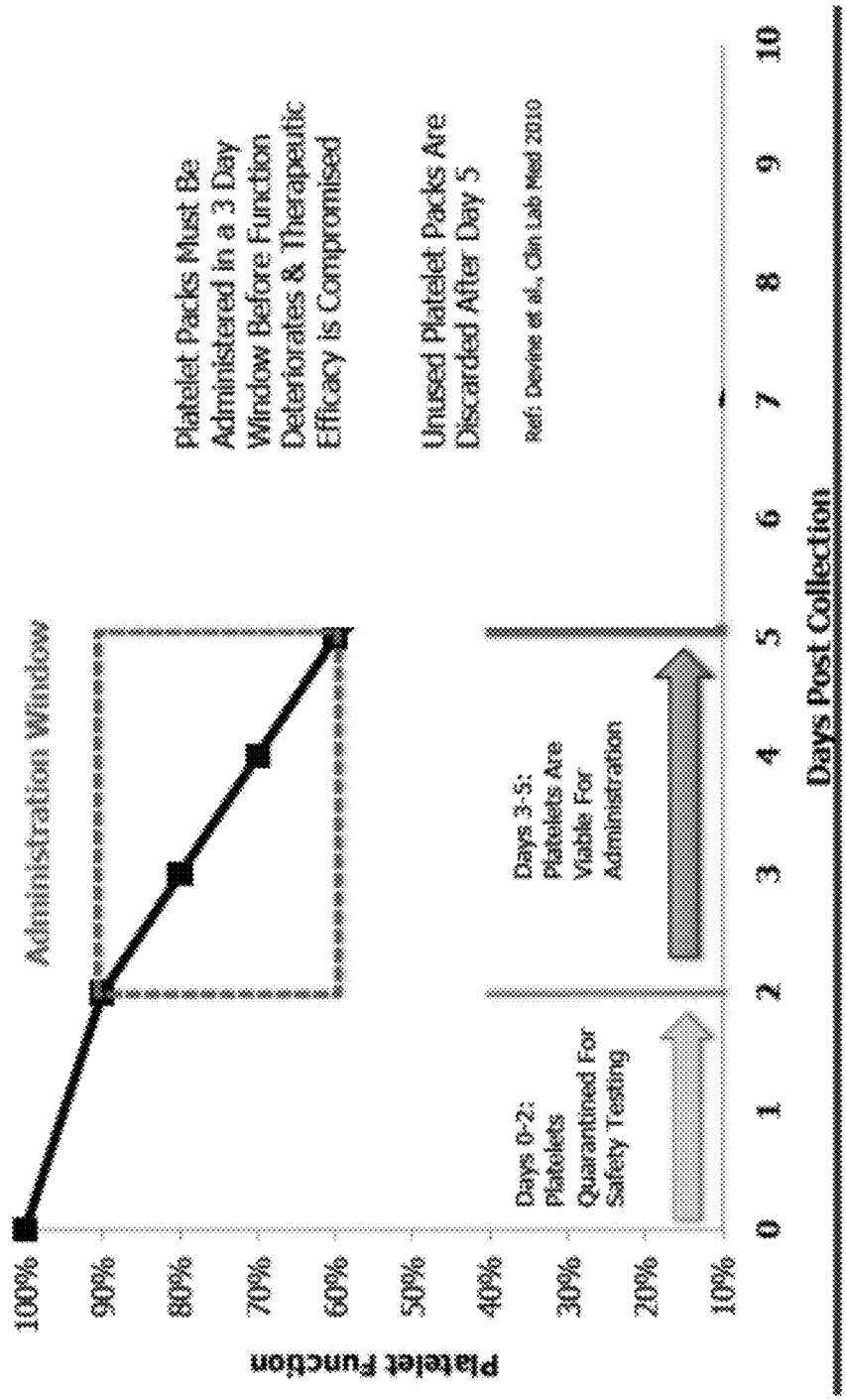
FIG. 4 Schematic depiction of the deterioration of platelet function over time when stored at room temperature.

SEQ ID NO: 1 is the sequence of OS-1, modified by the addition of a lysine residue, a cyclic peptide useful in the present invention when conjugated with a polymeric compound.

SEQ ID NO: 2 through 9 are the amino acid sequences of novel conjugated cyclic peptides useful in the present invention.

DETAILED DESCRIPTION OF THE INVENTION

Thus, the present invention provides methods and materials for treatment of thrombosis, thrombocytopenia and other platelet-related disorders using CCPs that are able to bind to GPIbα, in a non-covalent manner, thereby extending the stability storage of blood plasma components/platelets. More particularly, provided herein are methods and materials for extending the useful life for use of platelets and platelet containing compositions that are stored in temperatures below about 22° C.

DESCRIPTION OF EMBODIMENTS OF THE INVENTION

Compositions

In one aspect, the present invention provides cyclic conjugated peptides (CCPs) that are able to bind to GPIbα in a non-covalent manner. These CCPs may be useful to extend the useful storage life of platelets. The CCPs comprising an amino acid sequence selected from the group consisting of SEQ ID NO: 3, 4, 5, 6, 7, 8 or 9; or SEQ ID NO: 1 and 2, covalently linked with a polymeric compound. The resulting CCPs are tested to determine that they retain the ability to bind to GPIbα in a non-covalent manner, and that said CCPs exhibit enhanced inhibition of platelet binding to Mac-1 or Ashwell-Morell receptors compared to a cyclic peptide comprising the same amino acid sequence, which lacks a covalently linked polymeric compound.

In particular embodiments, the polymeric compound is a polyethylene glycol. In preferred embodiments, the polyethylene glycol has a molecular weight of between about 300 and 150,000 daltons, preferably between about 300 and 50,000 daltons, and most preferably between about 1000 and 50,000 daltons. The polyethylene glycol polymer may be branched. See DeNardo et al., Clinical Cancer Research, 9:3854-64s (2003).

Methods

In another aspect, the present invention provides methods for increasing the useful storage life of platelets. The methods comprise storing platelets with a cyclic conjugated peptide comprising the amino acid sequence of SEQ ID NO: 3 to 9, or SEQ ID NO: 1 or 2, covalently linked with a polymeric compound. The cyclic conjugated peptide has the ability to bind to GPIbα in a non-covalent manner, and said cyclic conjugated peptide exhibiting enhanced inhibition of platelet binding to Mac-1 or Ashwell-Morell receptors compared to a cyclic peptide comprising the same amino acid sequence, without a covalently linked polymeric compound. In certain embodiments, the platelets are stored at temperatures below 22° C. In preferred embodiments, the platelets are stored at temperatures of from about 0° C. to about 4° C.

In some embodiments, the platelets may be stored for 2 to 7 days at temperatures below 22° C. In preferred embodiments, the platelets may be stored for 5 to 7 days at temperatures below 22° C. In other preferred embodiments, the platelets may be stored for 2 to 7 days at temperatures of from about 0° C. to about 4° C. In preferred embodiments, the platelets may be stored for 5 to 7 days at temperatures of from about 0° C. to about 4° C.

The present inventors theorized that treatment of platelets with conjugated CCPs can result in significantly enhanced useful storage life for platelets which have been refrigerated or subject to cold-storage. Additional benefits may include the improved available supply of platelets and other plasma products, as well as improved safety as platelets and other fresh plasma products may be stored at colder temperatures to reduce the risk of pathogenic contamination. Characterization and biological investigations of stored platelets and use of current storage technologies may be employed. (Devine, Clin Lab Med 30:475-87 (2010)).

Together, these establish the potential use of the present invention for extending useful half-life/storage of platelets and platelet containing serum or blood plasma. The compositions and methods of the present invention may also be used in a clinical setting. For example, the methods and compositions of the present invention may be useful for the treatment and/or prevention of thrombosis, vascular inflammation, thrombocytopenia and other platelet-related disorders.

Thus, in other aspects, the present invention comprises methods of treating a subject who is suffering from thrombosis, vascular inflammation, thrombocytopenia or other platelet-related disorders, the method comprising treating ex vivo isolated platelets from one or more donors with a CCP of the present invention, and then administering to said subject these allogeneic platelets that have been treated with CCP (allogeneic platelet treatment and transfusion). Such treatment and transfusions may be useful for reduction of poor responses or refractoriness to allogeneic platelet transfusion (Slichter, Hematology 2007:172-78 (2007)).

In other embodiments, the methods of the present invention comprise preventing, avoiding or reducing thrombosis, vascular inflammation, thrombocytopenia or other platelet-related disorders in a subject, the method comprising treating ex vivo the same subject's platelets with a CCP of the present invention; and administering to said subject the platelets that have been treated with CCP said same subject the autologous platelets that have been treated with CCP (autologous platelet treatment and transfusions). Such treatment and transfusions may be useful for reduction of poor responses or refractoriness to autologous platelet transfusion (Slichter, Hematology 2007).

In other embodiments, the methods of the present invention comprise preventing or treating, or a method of avoiding or reducing thrombosis, vascular inflammation, or another platelet related disorder or disease in a subject, comprising administering to said subject an effective amount of a composition comprising a CCP of the present invention.

In preferred embodiments, the CCP is administered in combination with one or more VWF antagonists. The VWF antagonist is preferably selected from the group consisting of AJW200, a humanized monoclonal antibody to von Willebrand's Factor (Kageyama et al., Arteriosclerosis, Thrombosis and Vascular Biology, 22:187 (2002)), ARC-1779, a synthetically manufactured modified DNA/RNA aptamer conjugated to PEG (molecular weight 20 KDa) moiety at the 5' terminus, which binds to the A1 domain of von Willebrand's Factor with high affinity. (Cosmi, Curr Opin Mol Ther, 11:322-28 (2009)), ALX-0081, a bivalent nanobody which specifically targets the GpIb-binding site of von Willebrand's Factor (Bartunek et al., Circulation, 118:S656 (2008)), ALX-0681, a therapeutic nanobody targeting the A1-domain of von Willebrand's Factor (Majidi et al., Human Antibodies, 18:81-100 (2009)) or GPG-290, a chimeric GPIb-alpha protein/vWF antagonist, which blocks the interaction of endogenous GPIb-alpha with von Willebrand's Factor. (Wadanoli et al., Thromb. Haemost., 98:397-405 (2007)) or GPIbα-Ig variant fusion polypeptides. (Shaw et al., U.S. Pat. No. 7,727,535). The disclosure of these documents is hereby specifically incorporated by reference into the specification.

In other preferred embodiments, the CCP is administered in combination with one or more thrombopoietin (TPO) mimetics or TPO receptor agonists. Suitable TPO mimetics and/or TPO receptor agonists include the approved drugs PROMACTA® (eltrombopag) (GlaxoSmithKline, Inc.); and NPLATE® (romiplostim) (Amgen, Inc.). Other TPO mimetics and/or TPO receptor agonists that may be useful in the present invention also include those described in U.S. Pat. No. 7,169,931 (Takemoto et al., Shionogi & Co.); U.S. Pat. No. 7,488,590 (Feige et al., Amgen, Inc.) (and related PCT patent publications WO2001/83525 and WO2002/024782); U.S. Pat. No. 6,498,155 (Luengo and Lamb, GlaxoSmithKline); U.S. Pat. No. 7,786,159 (Spencer and Punnonen, Strategics, Inc.); and in PCT patent publication WO2004/026332 (Kaushansky and MacDonald; Johnson & Johnson); PCT patent publication WO2009/148954 (Yurklow and Shukla; Johnson & Johnson). The disclosure of these documents is hereby specifically incorporated by reference into the specification.

CCP Peptides

In certain embodiments, the pharmaceutical compositions comprise a full-length CCP-014 peptide [Ac-A C T E R M A L H N L C G G-NH$_2$ (SEQ ID NO: 1) or Ac-A C T E R M A L H N L C G G K-NH$_2$ (SEQ ID NO: 2)] and a pharmaceutically acceptable carrier suitable for administration to an individual. In certain embodiments, the pharmaceutical compositions comprise full-length CCP-014 peptide (SEQ ID NO: 1 or SEQ ID NO: 2) and a pharmaceutically acceptable carrier suitable for administration to an individual. In certain embodiments, the pharmaceutical compositions comprise a biologically-active fragment of CCP-014 peptide comprising and a pharmaceutically acceptable carrier suitable for administration to an individual. In certain embodiments, the pharmaceutical compositions comprise a biologically-active fragment of a full-length CCP-014 peptide comprising Ac-A C T E R M A L H N L C G G-NH$_2$(SEQ ID NO: 1) or Ac-A C T E R M A L H N L C G G K-NH$_2$(SEQ ID NO: 2) conjugated to PEG and a pharmaceutically acceptable carrier suitable for administration to an individual.

In certain embodiments, the invention comprises molecules in which the CCP-014 peptide is modified by the addition of physiologically compatible polymeric compounds, such as polyethylene glycol. The polymeric compound is covalently bound to an amino acid residue of the CCP peptide, generally a lysine residue. If desired, the amino acid sequence of a peptide can be modified by substitution of one or more amino acid residues with lysine, and/or by the addition of one or more lysine residues, to provide a convenient site for conjugation of the polymeric compound.

Preferred polymeric compounds for use in the present invention include monofunctional amino-reactive polyethylene glycol (PEG) polymers having molecular weights between about 400-5,000 Daltons, and can be chemically conjugated to reactive amine sites on CCP peptides. PEG polymers suitable for use in the present invention, and methods for their preparation and conjugation to peptides are described, for example, in U.S. Pat. No. 7,030,278; U.S. Pat. No. 6,956,135; U.S. Pat. No. 6,916,962; U.S. Pat. No. 6,541,543; U.S. Pat. No. 5,990,237; U.S. Pat. No. 5,252,714; US Patent Application 2010/0010194; PCT Patent Application WO2009/114151; and PCT Patent Application WO2001/024831.

PEG reagents that form stable amide linkages such as N-Hydroxy-succinimide or propionaldehyde PEG derivatives, as known in the art, are conjugated to CCP peptides.

```
                                             (SEQ ID NO: 3)
CTERZALHNLC(X)_N K-peg (SEQ ID NO: 4)
(J)_N CTERZALHNLC(X)_N K-peg (SEQ ID NO: 5)
peg-(J)_N CTERZALHNLC(X)_N (SEQ ID NO: 6)
peg-(J)_N CTERZALHNLC(X)_N-peg
J = any amino acid except C
Z = M, D, L, W or A
X = any amino acid except C
N = 1-10
peg = polyethyleneglycol
```

Examples of conjugated CCPs useful in the present invention include:

```
                                             (SEQ ID NO: 7)
ACTERMALHNLCGGG-peg (SEQ ID NO: 8)
peg-GCTERDALHNLCGGGG (SEQ ID NO: 9)
peg-ACTERMALHNLCSSG-peg
```

Munday et al. mapped a critical binding site for Mac-1 to GPIbα sequence Arg 218 to 224, a distinct site from VWF binding site. Munday et al., Blood (ASH Annual Meeting Abstracts) 114:472 (2009). Munday et al. proposed that a peptide corresponding to this region would therefore inhibit GPIbα binding to Mac-1, but block neither platelet adhesion to immobilized VWF nor thrombin-induced platelet aggregation, and could therefore specifically inhibit leukocyte-platelet complexes that promote vascular inflammation. Thus, the GPIbα binding sites to Mac-1 and VWF are distinct and can be independently blocked.

Without being bound by any specific theory, it is believed that there are multiple mechanism by which CCPs prevent platelet clearance. The first mechanism is likely through preventing the protein-protein binding of Mac-1 via allosteric effects caused by the CCP at the GPIbα protein binding site. The second mechanism is likely by steric hinderance or shielding, caused by the presence of a conjugated PEG polymer, preventing the interaction between components of the N-linked glycans on GPIbα and the lectin-like receptors such as the Ashwell-Morell or Mac-1 receptors. A third mechanism by which CCPs can prevent platelet clearance is through the inhibition of the binding of VWF and GPIbα. VWF binding has been implicated as a contributing event in the rapid clearance of cold stored platelets. See Rumjantseva et al., Transfusion and Apheresis Science 42:63-70 (2010). A fourth mechanism by which CCPs can prevent platelet clearance is by preventing morphological changes and microaggregation of platelets (Maurer et al., US Patent application 2009/0041737)

Compositions and Formulations:

In certain embodiments, the composition further comprises one or more surfactants. Exemplary surfactants include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the surfactant is a Tween surfactant (e.g., Tween 60, Tween 80, etc.).

In certain embodiments, the composition further comprises one or more preservatives. Exemplary preservatives may include antioxidants, chelating agents, antimicrobial preservatives, antifungal preservatives, alcohol preservatives, acidic preservatives, and other preservatives.

In certain embodiments, the one or more preservative comprises an antioxidant. Exemplary antioxidants include, but are not limited to, phosphites, dibutyl phosphite, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, sodium sulfite, cysteine hydrochloride, thioglycerol, sodium mercaptoacetate, sodium formaldehyde sulfoxylate (SFS), lecithin, and alpha-tocopherol. In certain embodiments, the antioxidant is dibutyl phosphite or sodium bisulfite ($NaHSO_3$).

In certain embodiments, the one or more preservative comprises a chelating agent. Exemplary chelating agents include, but are not limited to, ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

In certain embodiments, the one or more preservative comprises an antimicrobial preservative. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

In certain embodiments, the one or more preservative comprises an antifungal preservative. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid.

In certain embodiments, the one or more preservative comprises an alcohol preservative. Exemplary alcohol preservatives include, but are not limited to, ethanol, polyethylene glycol, phenol, phenolic compounds, bisphenol, chlorobutanol, hydroxybenzoate, and phenylethyl alcohol.

In certain embodiments, the one or more preservative comprises an acidic preservative. Exemplary acidic preservatives include, but are not limited to, vitamin A, vitamin C, vitamin E, beta-carotene, citric acid, acetic acid, dehydroacetic acid, ascorbic acid, sorbic acid, and phytic acid.

Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

In certain embodiments, the composition further comprises one or more diluents. Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

In certain embodiments, the composition further comprises one or more granulating and/or dispersing agents. Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

In certain embodiments, the composition further comprises one or more binding agents. Exemplary binding agents include, but are not limited to, starch (e.g. cornstarch and starch paste); gelatin; sugars (e.g. sucrose, glucose, dextrose, dextrin, molasses, lactose, lactitol, mannitol, etc.); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

In certain embodiments, the composition further comprises one or more buffering agents. Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

In certain embodiments, the composition further comprises one or more lubricating agents. Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

In certain embodiments, the composition further comprises one or more solubilizing or suspending agents. Exemplary solubilizing or suspending agents include, but are not limited to, water, organic solvents, oils, and mixtures thereof. Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof. In certain embodiments, the oil is mineral oil.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

The formulations of the pharmaceutical compositions described herein may be prepared by any method known or hereafter developed in the art of pharmacology. In general, such preparatory methods include the step of bringing the active ingredient (i.e., a glycosylated deltorphin variant) into association with a carrier and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) of the active ingredient.

Preferred dosage forms include oral and parenteral dosage forms. Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Compositions for oral administration are typically liquid or in solid dosage forms. Compositions for oral administration may include protease inhibitors, including organic acids such as citric acid, in order to inhibit pancreatic and brush border proteases. Compositions for oral administration may additionally include absorption enhancers, such as acylcarnitine and lauroylcarnitine, to facilitate the uptake of the peptide through the lumen of the intestine into the systemic circulation by a paracellular transport mechanism. Compositions for oral administration may additionally include detergents to improve the solubility of the peptides and excipients and to decrease interactions with intestinal mucus. Solid form compositions for oral administration, such as tablets or capsules, may typically comprise an enteric coating which further protects the peptides from stomach proteases and permits passage of the tablet or capsule into the small intestine. The solid form composition may additionally comprise a subcoat such as a non-ionic polymer. Examples of preparation of such orally available formulations are disclosed in U.S. Pat. No. 5,912,014, U.S. Pat. No. 6,086,918 and U.S. Pat. No. 6,673,574. The disclosure of each of these documents is hereby incorporated herein by reference.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, comprise 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* 21$^{st}$ ed., Lippincott Williams & Wilkins, 2005.

The skilled clinician will be able to determine the appropriate dosage amount and number of doses of an agent to be administered to subject, dependent upon both the age and weight of the subject, the underlying condition, and the response of an individual patient to the treatment. In addition, the clinician will be able to determine the appropriate timing for delivery of the agent in a manner effective to treat the subject. Preferably, the agent is delivered within 48 hours prior to exposure of the patient to an amount of a thrombosis or thrombocytopenia provoking stimulus effective to induce thrombosis or thrombocytopenia, and more preferably, within 36 hours, and more preferably within 24 hours, and more preferably within 12 hours, and more preferably within 6 hours, 5 hours, 4 hours, 3 hours, 2 hours, or 1 hour prior to exposure of the patient to an amount of thrombosis or thrombocytopenia provoking stimulus effective to induce thrombosis or thrombocytopenia. In one embodiment, the agent is administered as soon as it is recognized (i.e., immediately) by the subject or clinician that the subject has been exposed or is about to be exposed to a thrombosis or thrombocytopenia provoking stimulus, and especially a thrombosis or thrombocytopenia provoking stimulus to which the subject is sensitized. In another embodiment, the agent is administered upon the first sign of development of thrombosis or thrombocytopenia, and preferably, within at least 2 hours of the development of symptoms of thrombosis or thrombocytopenia, and more preferably, within at least 1 hour, and more preferably within at least 30 minutes, and more preferably within at least 10 minutes, and more preferably within at least 5 minutes of development of symptoms of thrombosis or thrombocytopenia. Symptoms of thrombosis or thrombocytopenia and methods for measuring or detecting such symptoms have been described and are well known in the art. Preferably, such administrations are given until signs of reduction of thrombosis or thrombocytopenia appear, and then as needed until the symptoms of thrombosis or thrombocytopenia are gone.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Still further encompassed by the invention are kits that comprise one or more inventive complexes and/or compositions. Kits are typically provided in a suitable container (e.g., for example, a glass, foil, plastic, or cardboard package). In certain embodiments, an inventive kit may include one or more pharmaceutical excipients, pharmaceutical additives, therapeutically active agents, and the like, as described herein. In certain embodiments, an inventive kit may include means for proper administration, such as, for example, graduated cups, syringes, needles, cleaning aids, and the like. In certain embodiments, an inventive kit may include instructions for proper administration and/or preparation for proper administration.

EXAMPLES

PEG polymers can be modified by various functional groups (see Harris et al., Clin Phamacokinet, 40:539-551 (2001) and the amino terminal end of CCPs or other linking amino acids, such as lysine residues present in the CCP, can be linked thereto. By "pegylated CCP" is meant a CCP having a polyethylene glycol moiety covalently bound to an amino acid residue or linking group of the peptide backbone of the CCP.

Isolation of Platelets for Labeling with CM-Orange

Blood is drawn from consenting normal human volunteers by venipuncture into 0.1 volume of Aster-Jandl citrate-based anticoagulant (Hartwig and DeSisto, J. Cell Biol., 407-425 (1991)) and platelet rich plasma (PRP) is prepared by centrifugation of the anticoagulated blood at 300×g for 20 min at room temperature. Platelets are separated from plasma proteins by gel-filtration at room temperature through a small Sepharose 2B column (Hoffmeister et al., Biol. Chem. 276, 24751-24759 (2001)). Platelets used in the in vitro THP-1 cell or HepG2 binding & phagocytosis assays described below are labeled with 1.8 uM CellTracker™ Orange CMTMR (CM-Orange) for 20 min at 37° C. (Brown et al., J. Biol. Chem. 275, 5987-5995 (2000)), and unincorporated dye was removed by centrifugation (850×g, 5 min) with 5 volumes of washing buffer containing 140 mM NaCl, 5 mM KCl, 12 mM trisodium citrate, 10 mM glucose, and 12.5 mM sucrose, 1 ug/ml $PGE_1$, pH 6.0 (buffer A). Platelets were resuspended at $3×10^8$/ml in a solution containing 140 mM NaCl, 3 mM KCl, 0.5 mM $MgCl_2$, 5 mM $NaHCO_3$, 10 mM glucose and 10 mM Hepes, pH 7.4 (buffer B).

Platelet Preparation

Human venous blood is collected from healthy volunteers by venipuncure into one-tenth of the blood volume of Aster Jandl citrate-based anticoagulant (85 mM sodium citrate, 69 mM citric acid, 111 mM glucose, pH 4.6). See Rumjantseva et al., Nature Medicine, 15:1273-80 (2009).

Platelet-rich plasma (PRP) is prepared by centrifugation at 268 g for 20 min at 22° C. For long-term storage experiments, human platelet concentrates are stored at 4° C. for up to 10 days without agitation. PRP samples (3 ml) are obtained under sterile conditions at days 0, 2, 5 and 10. Platelets are collected from the PRP by centrifugation at 834 g for 5 ml, washed in platelet buffer (140 mM NaCl, 5 mM KCl, 12 mM trisodium citrate, 10 mM glucose, 12.5 mM sucrose 1 ug/ml $PGE_1$, pH 6.0)(buffer A) and resuspended in 10 mM HEPES, 140 mM NaCl, 3 mM KCl, 0.5 mM $MgCl_2$, 10 mM glucose and 0.5 mM $NaHCO_3$, pH 7.4 (buffer B). See Rumjantseva et al., Nature Medicine, 15:1273-80 (2009)

Platelet Temperature and Storage Protocols

Isolated platelets are chilled for 2 hrs at ice-bath temperatures, a process designated as short term cooling (or as 0° C.), or are resuspended in platelet-poor plasma and stored for 48 hr at 4° C., designated as long-term refrigeration (or as 4° C.). All cooled and refrigerated platelets are rewarmed for 15 min at 37° C. before use. With the exception of Indium$^{111}$ labeling, all labeling procedures and enzymatic digestion of platelets are performed before storage. Freshly isolated platelets, maintained for a maximum of 2 hrs at 22° C. are used as controls for all survival experiments, and are designated as fresh platelets (or as 22° C.). Rumjantseva et al., Nature Medicine, 15:1273-80 (2009).

Histology

Mice are infused with $3×10^9$ biotinylated platelets. Organs are collected 5, 15 and 30 mins and 24 hrs afterward, fixed in paraformaldehyde and embedded in paraffin and sectioned every 3 um. Distribution of biotinylated platelets is visualized with streptavidin-peroxidase conjugate and the ImmunoHisto Peroxidase Detection Kit (Pierce). Sections are counterstained with H&E according to the manufacturer's recommendations. Quantitative analysis of staining is done in blinded samples. Ten tissue sections from mice having similar levels of injected platelets are selected and scored for hepatocytes and macrophages containing biotinylated platelets. See Rumjantseva et al., Nature Medicine, 15:1273-80 (2009)

Macrophage Depletion

Mice are depleted of phagocytic cells by a single injection of liposomes containing dichloromethylene bisphosphonate (clodronate liposomes). Control liposomes are prepared with PBS in place of condronate. Mice are injected intravenously with 0.02 ml of clodronate liposomes or control liposomes per 10 g body weight 24 hrs before platelet transfusion. This treatment depletes 99% of Kupffer cells and 95% of splenic macrophages. Macrophages are stained with an antibody to mouse F4/80 (SEROTEC, clone CI:A3-1) in tissue sections of clodronate-treated and untreated mice. See Rumjantseva et al., Nature Medicine, 15:1273-80 (2009).

Multi-Distance Spatial Cluster Analysis (Ripley's K-Function)

K-function analysis is used to determine whether GPIbα distribution is random, clustered or dispersed on the membrane of cold versus room-temperature platelets. GPIbα is visualized with immunogold, x and y coordinates are measured and L(r)-r versus the radius r is plotted. Values less than −1 indicate significant dispersal, whereas values greater than 1 indicate significant clustering. See Rumjantseva et al., Transfusion and Apheresis Science 42:63-70 (2010).

In Vitro Platelet Phagocytic Assay Using Stimulated THP-1 Cells (Mac-1 Mediated Binding)

THP-1 cells are obtained from ATCC (ATCC #TIB-202). Differentiated THP-1 phagocytic cells ($1 \times 10^6$ cells/ml) are activated by the addition of 150 pg/ml phorbol 12-myristate 13-acetate for 15 min at 37° C. and plated onto human albumin (1 mg/ml)-coated 24-well plates ($1 \times 10^6$ cells/well) and allowed to adhere for 45 min at 37° C. in RPMI 1640 medium. The cells are washed and maintained in Hanks' balanced salt solution (HBSS) (Cellgro, Mediatech) containing $Ca^{2+}Mg^{2+}$ or alternatively HBSS without $Ca^{2+}Mg^{2+}$ containing 2 mM EGTA and 2 mM EDTA to determine the effects of divalent cations on platelet phagocytosis.

CM-Orange-labeled RT or chilled platelets ($5 \times 10^8$ cells/ml) are pre-incubated for 5 min with CCPs diluted to concentrations ranging from 0.1 nM to 100 nM, then added to the THP-1 cells for 30 min at 37° C. under gentle agitation. Surface-associated platelets are removed through digestion with 0.05% trypsin-EDTA (Invitrogen) followed by the addition of trypsin inhibitors for 5 min. THP-1 cells are detached from the wells and incubated with FITC-anti-CD61 mAb, which recognizes the platelet-specific β3 integrin (Product # BYA9203-1 Accurate Scientific Corp., Westbury, N.Y.). Platelet ingestion is determined and quantified by flow cytometry on a FACSCalibur flow cytometer (BD Biosciences). Data is acquired in log 10 fluorescence. The percentage of phagocytes positive for CM-Orange fluorescence when incubated with RT platelets is set to one in order to calculate the ratio of the phagocytic increase for the chilled platelet population.

Construction of Mac-1 Transfected Mammalian Cells and their Cultivation:

Chinese hamster ovary (CHO) or HEK-293 cell lines (ATCC Manassas, Va.) are generated that express functional recombinant human Mac-1 receptor on the cell surface. Isolated cDNA encoding $α_M$ chain (CD11b) is cloned into the expression vector pcDNA3, isolated cDNA encoding $β_2$ integrin (CD18) is cloned into pZeoSV. Superfect™ transfection reagent (Qiagen, Hilden, Germany) is used for cell transfection. Clones are selected for resistance against 700 μg/ml G418 (Geneticin®, Gibco, Eggenstein, Germany) and 250 μg/ml Zeocin® (Invitrogen, Karlsruhe, Germany) and by the flow cytometric detection of CD11b and CD18 epitopes. Clones used in further experiments should contain identical expression levels of CD11b or CD18 as determined by flow cytometry and can be further examined by RT-PCR and immunoprecipitation to prove the correct expression of Mac-1. Transfected cells are maintained in Dulbecco's modified Eagle medium (DMEM), 10% (vol/vol) fetal calf serum (FCS), 100 U/ml penicillin and 100 μg/ml streptomycin. All culture media are from GIBCO (Eggenstein, Germany), and the cell culture plastic was from Nunc (Roskilde, Denmark).

Adhesion Assay of Platelets to Mac-1 Expressing Cells

CHO cells expressing Mac-1 are seeded on a VenaFux™ platform (Cellix LTD, Dublin). Approximately $2.5 \times 10^6$ human platelets in PRP are incubated for 5 min with control buffer or buffer with CCPs diluted to concentrations ranging from 0.1 nM to 100 nM. Treated platelets are then infused into VenaFux™ platform according to the manufacturer's protocol and platelet adhesion events are quantified by the Cellix image analysis software.

Adhesion Assay of Mac-1 Bearing Cells to Immobilized GPIbα

THP-1 cells or alternatively CHO or 293 cells expressing Mac-1 are harvested with cell-dissociating buffer (Life Technologies) for 1 minute at 22° C., washed twice, resuspended in serum-free media, and loaded with BCECF AM [2',7'-bis-(2-carboyethyl)-5-(and-6)-carboxyfluorescein, acetoxymethyl ester] (1 umol/L) according to the manufacturer's protocol (Molecular Probes). Cells ($10^5$ per well) are placed in 48-well tissue culture plates (Costar) coated with 200 uL of 5 nmol/L fibrinogen or 50 nmol/L sGPIb (R&D Systems, Minneapolis Minn. Cat #4067-GP) overnight at 4° C. and then blocked with 0.5% polyvinylpyrrolidone for 1 hour at room temperature. Coated plates are then incubated for 5 min with CCPs diluted to concentrations ranging from 0.1 nM to 100 nM. Adhesion to cells with Mac-1 is stimulated with phorbol 12-myristate 13-acetate (PMA) (20 ng/mL) in the presence of 2 mmol/L $Mg_2$. Plates are washed with 0.9% NaCl (3 to 5 times), and adhesion was quantified by measuring the fluorescence of BCECF AM-loaded cells with a Cytofluor II fluorescence multiwell microplate reader (PerSeptive Biosystems).

In Vitro HepG2-Based Platelet Ingestion Assay (Ashwell-Morrell Mediated Binding)

Human HepG2 hepatocarcinoma cells (ATCC HB-8065) are maintained in αMEM (GIBCO Invitrogen), 2% heat-inactivated bovine calf serum (BCS), 3% standard fetal bovine serum (FBS), and 1% of a penicillin and streptomycin solution composed of 10,000 U ml-1 penicillin G and 10 mg ml-1 streptomycin sulphate. HepG2 cells express Ashwell-Morrell receptors similar to human hepatocytes, but do not express Mac-1 receptors. HepG2 cells are not passaged >2 times before use.

For assays, the HepG2 cells are transferred to 24-well plates ($10^6$ per well), allowed to adhere for 24 h, and starved for 30 min by replacing αMEM media without serum. Cytochalasin D (SIGMA) is diluted into αMEM media at the indicated concentrations and added to the HepG2 cells. DMSO is used as control. CCPs at 10 fold diluted concentrations from 0.1 nM to 100 nM are mixed $1 \times 10^8$ CM-Orange-labeled platelets (fresh, at 22° C. platelets or platelets cooled at 0° C. or 4° C.) per well, with or without cytochalasin D. HepG2 cells and platelets are then incubated for 5-30 min at 37° C. with gentle agitation. After the incubation period, the HepG2 monolayers are washed 3 times by removing and changing the buffer. HepG2 cells are dissociated from the wells with 0.05% trypsin, 0.53 mM EDTA in HBSS (GIBCO Invitrogen) at 37° C. for <10 min. CM-Orange-labeled platelet ingestion (phagocytosis) is quantified by flow cytometry. HepG2 cells are gated according to their forward and side scatter characteristics. HepG2 cells with ingested platelets acquired orange fluorescence. Platelets adherent to HepG2 cell surfaces are labeled with the FITC conjugated antibody to human CD61 (Beckon-Dickinson). CM-Orange-labeled cells are counted. Approximately 10,000 events can be acquired for each sample.

Von Willebrand Factor Binding Assay

Platelet bound VWF was detected by incubating 3 μl of FITC-conjugated antibody to human or mouse VWF, or with non-immune rabbit polyclonal IgG (control), with $2.5 \times 10^6$ human platelets in PRP for 20 min at room temperature after platelets have been incubated for 5 min with control buffer or buffer with CCPs diluted to concentrations ranging from 0.1 nM to 100 nM. Labeled samples were analyzed by flow cytometry after dilution into buffer. Data is expressed as % positive cells determined for VWF compared to the appropriate IgG negative control.

Human Platelet Studies

The following human platelet studies are conducted using procedures from Wandall et al., Blood 111:3249-56 (2008) are adapted as follows.

Optimization of the CCP-Treatment of Platelets.

Aliquots (2 mL) of nonwashed human apheresis platelets ($1-2\times10^9$ platelets/mL) are incubated with increasing concentrations (0.00 mM to 1.50 mM at 0.25 mM increments) of CCP for time periods of 0 to 90 minutes at 15 minute increments at 37° C. Platelets are washed, and the platelets are assessed for maximal RCA-1 binding and minimal sWGA binding using varying concentrations of CCP and time of incubation.

In Vivo Studies.

Human studies are conducted with the approval of an institutional review board and a radiation safety committee after obtaining informed consent from all volunteers in accordance with the Declaration of Helsinki Volunteers must meet standard donation criteria, and must not have taken any medication known to alter platelet function for 14 days before platelet donation.

A PFA-100 assay (Siemans USA, Deerfield Ill.), is performed with human blood collected into vacutainer tubes, containing 3.2% sodium citrate as the anticoagulant, from volunteers who had not taken any platelet inhibitory medications over the previous two weeks. A 5 µl aliquot of CCP dissolved in 25% DMSO is added to 1 ml of whole human blood to give a final CCP concentration ranging from 0.1 nM to 100 nM and a final DMSO concentration of 0.125%. Tubes are inverted 10 times to mix, and allowed to sit at room temperature for 5 m prior to analysis with the PFA-100 instrument. Collagen/epinephrine cartridges (Siemans USA, Deerfield, Ill.) are used for the PFA-100 assay following the manufacturer's protocol. Closure times of 80±4 seconds are typically obtained with 0.125% DMSO alone in whole blood.

The study is an open-label, controlled phase 1 study using standard radiolabeled autologous platelet transfusion protocols to determine platelet recoveries and survivals. Holmes et al., Brit. J. Haematol. 84:717-23 (1993). Three platelet products—each stored for 48 hours—are evaluated: (1) platelets stored at 4° C. that were treated with CCP ("CCP-treated cooled"); (2) control platelets stored at 4° C. without CCP treatment ("untreated cooled"); and (3) control platelets stored at 22° C. without CCP treatment ("untreated room temperature" or "RT").

Healthy volunteers are enrolled, and each donatee apheresis platelets on a Haemonetics MCS+ apheresis machine (Haemonetics, Braintree, Mass.). Platelets are collected into one bag, and then divided into 2 bags of approximately 120 mL. CCP is supplied in 0.9% saline to produce a 40 mM sterile filtered solution filled into 5-mL plastic syringes. Aseptic media fill validation is conducted as a part of the controls on the fill and finish operation. The stock solution is kept at 4° C. throughout the process and storage and stability of the CCP is verified. Immediately after collection, one bag of platelets from each donor is treated with CCP by sterile docking the CCP container onto a platelet storage bag. After addition of CCP, the CCP-treated platelets are incubated for 1 hour at 37° C. with agitation and then stored at 4° C. for 36 to 48 hours without agitation. The other bag of platelets serves as a control and is incubated without CCP treatment for 1 hour at 37° C. with agitation, followed by storage for 36 to 48 hours either without agitation at 4° C. or with agitation at 22° C.

The bags of platelets from each individual donor are radiolabeled as described in Holmes et al., Br J Haematol, 84:717-23 (1993) with a different radioactive isotope, either $^{51}$Chromium or $^{111}$Indium, and 5 mL to 10 mL of both the radiolabeled test and control platelets are simultaneously transfused back to their donor. Radioisotopes used for labeling are alternated between test and control platelets to avoid bias related to the isotope used for radiolabeling. Blood samples are drawn before and at 2 hours, 1, 2, 3, 5, 7, and 10 days after transfusion, and the posttransfusion recovery and survival of the platelets are determined using the COST program, described in Lotter et al., Comput Biol Med; 18:305-15 (1988). Samples are obtained to correct for elution of either radioisotopic label and for any residual radioactivity bound to red cells. The recovery and survival data are reported both uncorrected for label elution or residual activity, as well as corrected for these 2 parameters.

During and for 2 hours after each platelet infusion, subjects are carefully monitored for vital signs and potential adverse reactions. Follow-up visits are conducted at days 1, 2, 3, 5, 7, 10, 14, and 90. Vital signs are obtained at each visit, and the subjects are queried about the occurrence of any adverse events. Additional telephone interviews to document any long-term adverse events are conducted on days 28, 42, 56, and 70 after infusion.

In Vitro Testing of the Human Platelet Preparations.

Baseline and at days 14 and 90 after infusion, samples are taken from each volunteer to detect IgG and IgM antiplatelet antibodies. Platelets with and without CCP treatment are incubated with each volunteer's plasma and with the Fab'2 fraction of FITC-conjugated goat antibody to the Fc chain of human IgG and IgM (Jackson Laboratories, Bar Harbor, Me.). Binding of conjugated Fab'2 fragments is monitored by FACS analysis (FACScan; Becton Dickinson Biosciences). Plasma with known HLA antibodies is used as a positive control.

Samples are collected on days 0 and 2 from the stored platelets for the following measurements. Blood gas and pH measurements using a blood gas analyzer (Bayer, East Walpole, Mass.). Glucose and lactate are measured using an Abbott Aeroset Analyzer (Abbott, Round Lake, Ill.). Platelet counts and mean platelet volume (MPV) are performed on an ABX Micros particle counter (ABX, Montpellier, France). Morphology score is performed by the method of Kunicki et al., Transfusion; 15:414-21 (1975). Hypertonic shock response (HSR) and extent of shape change (ESC) are performed as described in Murphy et al., Transfus Med Rev; 8:29-36 (1994). CD62P expression is measured by FITC-labeled CD62P-specific monoclonal antibody S-12 using FACS analysis. Annexin V binding is determined by FACS analysis using fluorescently labeled annexin-V (Vybrant Assay Kit [V-13240]; Molecular Probes, Eugene, Oreg.). CCP-treatment is verified using fluorescently labeled RCA-1 and sWGA lectins with FACS analysis as described in Hoffmeister et al., Science, 301:1531-34 (2003).

Platelet aggregation and agglutination experiments are performed with a PLT aggregation profiler (Model PAP-; Bio/Data, Horsham, Pa.). Platelets are washed and resuspended as described in Babic et al., Transfusion; 47:442-51 (2007) and activated by adding 0.1 U to 1 U thrombin (Sigma-Aldrich, St Louis, Mo.) per mL; platelet-rich plasma (PRP) is mixed with platelet-poor plasma (PPP) in the ratio 1:1 and is then activated through the addition of 1.5 mg/mL ristocetin (Sigma-Aldrich) for 3 minutes at 37° C. under constant stirring (1000 rpm). Resuspension buffer for washed PLTs and PPP for PRP are set as maximum of light transmission.

In Vivo Safety of Infusion of Cold-Stored Human Platelets Treated with CCP.

The safety of transfused chilled CCP-treated platelets, along with any residual CCP, can be evaluated by regular clinical assessments, follow-up phone interviews, monitoring the subjects' platelet counts, and testing for the presence of antibodies against both CCP-treated and untreated platelets.

Platelet count in the storage bags is assessed before and after storage. Platelets are assessed at 1, 2, 4 days for CCP-treated 4° C.-storage, control 4° C.-stored, and control 22° C.-stored platelets. Overall, pH, $PCO_2$, $HCO_3$, glucose, P-selectin, and annexin V binding is measured.

The following procedured are adapted from Hoffmeister et al., US Patent Application 2008/0138791. Modest cooling primes platelets for activation, but refrigeration causes shape changes and rapid clearance, compromising storage of platelets for therapeutic transfusions. It has previously been shown that shape change inhibition does not normalize cold-induced clearance. It has also been shown that cooling platelets rearranges the surface configuration of the von Willebrand factor (VWF) receptor complex alpha subunit (GPIbα), such that it becomes targeted for recognition by complement receptor 3 receptors (CR3) predominantly expressed on liver macrophages, leading to platelet phagocytosis and clearance. GPIbα removal prolongs survival of unchilled platelets. Chilled platelets bind VWF and function normally in vitro and ex vivo after transfusion into CR3-deficient mice. Cooled platelets, however, are not "activated" like platelets exposed to thrombin or ADP, and their VWF-receptor complex reacts normally with activated VWF.

As the temperature falls below 37° C., platelets become more susceptible to activation by thrombotic stimuli, a phenomenon known as "priming" (Faraday and Rosenfeld, Anesthesiology, 88:1579-1585 (1998); Hoffmeister et al., J Biol Chem 276:24751-24759 (2001)). Priming may be an adaptation to limit bleeding at lower temperatures of body surfaces where most injuries occur. It has been proposed that the hepatic clearance system's purpose is to remove repeatedly primed platelets, and that conformational changes in GPIbα that promote this clearance do not affect GPIbα's hemostatically important binding to VWF. Therefore, selective modification of GPIbα may accommodate cold storage of platelets for transfusion.

This example compares the in vitro and in vivo hemostatic function of chilled, unmodified and chilled, CCP-treated platelets. Chilled platelets are not "activated" in the sense of agonist-stimulated platelets. Patients undergoing surgery under hypothermic conditions may develop thrombocytopenia or show severe hemostatic post-operative impairments. It is believed that under these hypothermic conditions, platelets might lose their functionality. However, when patients undergo hypothermic surgery, the whole organism is exposed to hypothermia leading therefore to changes in multiple tissues. Adhesion of non-chilled platelets to hepatic sinusoidal endothelial cells is a major mechanism of cold preservation injury (Takeda et al., Transplantation 27:820-28 (1999)). Therefore, it is likely that it is the interaction between cold hepatic endothelium and platelets, not platelet chilling per se, that leads to deleterious consequences under hypothermic conditions of surgery or transplantation of cold preserved organs (Upadhya et al, Transplantation 73:1764-70 (2002)).

Two approaches show that chilled platelets have hemostatic function. In one approach, the circulation of chilled platelets in $\alpha_M\beta2$ deficient mice facilitates studies of platelet function after cooling. In the other approach, the function of modified chilled and (presumably) circulating platelets is tested.

Murine platelets that express the human GPIbα chain are generated from transgenic mice (Ware et al., PNAS 97:2803-08 (2000)) and are herein referred to as "murine$^{TG}$" platelets. Human and murine$^{TG}$ unmodified and CCP-treated chilled platelets are tested for functionality, including in vitro aggregation to agonists, P-selectin exposure and fibrinogen binding.

$a_M b2$-deficient or wild-type mice are transfused with murine chilled or room temperature platelets, CCP-treated or not, and allowed to circulate for 30 min, 2 and 24 hours. It is determined whether chilled platelets contribute to clotting reactions caused by tail vein bleeding and if these platelets bind agents such as fibrinogen after activation. It is further determined how chilled platelets, CCP-treated or not, contribute to clotting on ferric chloride injured and exteriorized mouse mesenteries, an in vivo thrombus-formation model. This method detects the number of platelets adherent to injured vessels and has documented impaired platelet vessel wall interactions of platelets lacking glycoprotein V or β3-integrin function (Ni et al, Blood 98:368-73 (2001); Andre et al, Nat Med 8:247-52 (2002)). Finally, the storage parameters of the modified platelets are determined.

In vitro platelet function is compared using aggregation with thrombin and ADP and botrocetin induced VWF-binding to murine$^{TG}$ platelets. Murine$^{TG}$ and human chilled platelets CCP-treated or untreated platelets are normalized to a platelet concentration of $0.3\times10^9/mm^3$, and aggregation is induced using the various agonists according to standard protocols (Bergmeier et al., J. Biol. Chem., 276: 25121-26 (2001)). To study VWF-binding, murine VWF is activated using botrocetin and the binding of fluorescently labeled VWF to chilled platelets modified or not in PRP is analyzed (Bergmeier, Ibid). To evaluate whether degranulation of platelets occurs during CCP-treatment, P-selectin exposure of chilled murine$^{TG}$ and human platelets, CCP-treated or not, is measured using fluorescent labeled anti-P-selectin antibodies by flow cytometry as described in Michelson et al., Proc Natl Acad Sci, USA 93:11877-82 (1996).

$10^9$ CMFDA-labeled platelets are transfused into mice, first verifying that these platelets are functional in vitro. It is determined whether chilled platelets contribute to aggregation by transfusing chilled or room temperature CMFDA-labeled platelets into $\alpha_M\beta2$ deficient mice. At 30 min, 2 hours and twenty-four hours after the infusion of platelets, a standard tail vein bleeding test is performed as described in Denis et al, Proc Natl Acad Sci USA 95:9524-29 (1998). The emerging blood is fixed immediately in 1% formaldehyde and platelet aggregation is determined by whole blood flow cytometry. Platelet aggregates appear as bigger sized particles in the dot plot analysis. To verify that the transfused platelets do not aggregate in the normal circulation, the mice are also bled through the retroorbital eye plexus into an anticoagulant. Platelets do not form aggregates under these bleeding conditions. The emerging blood is fixed immediately and platelets are analyzed by flow cytometry in whole blood as described above. Platelets are identified through binding of a phycoerythrin-conjugated $\alpha_{IIb}\beta_3$ specific monoclonal antibody. The infused platelets in the blood sample are identified by their CMFDA-fluorescence. Non-infused platelets are identified by their lack of CMFDA fluorescence, per Michelson et al, Proc Natl Acad Sci USA 93:11877-82 (1996). The same set of tests is performed with CMFDA modified CCP-treated chilled platelets transfusing these platelets into $\alpha_M\beta_2$ and wild-type. This experiment tests aggregation of chilled platelets modified or not in shed blood.

$10^9$ CM-orange labeled unmodified chilled or room temperature platelets are transfused into $\alpha_M\beta_2$ deficient mice to verify that these platelets are functional in vitro. At 30 min, 2 h and twenty-four hours after the infusion of CM-orange labeled platelets, PRP is isolated as described and analyzed by flow cytometry. P-selectin exposure is measured using an anti FITC-conjugated anti P-selectin antibody as described in Berger et al, Blood 92:4446-52 (1998). Non-infused platelets are identified by their lack of CM-orange fluorescence. The infused platelets in the blood sample are identified by their CM-orange fluorescence. CM-orange and P-selectin positive platelets appear as double positive fluorescently (CM-orange/FITC) stained platelets. To verify that chilled platelets still expose P-selectin after thrombin activation, PRP is activated through the addition of thrombin (1 U/ml, 2 min at 37° C.) and P-selectin exposure is measured as described. To analyze the binding of fibrinogen to $\alpha_{IIb}\beta_3$, isolated platelets are activated through the addition of thrombin (1 U/ml, 2 min, 37° C.) and Oregon-green coupled fibrinogen (20 ug/ml) added for 20 min at 37° C. (Heilmann et al, Cytometry 17:287-93 (1994)). The samples are analyzed immediately by flow cytometry. The infused platelets in the PRP sample are identified by their CM-orange fluorescence. CM-orange and Oregon-green positive platelets appear as double positive fluorescently stained (CM-orange/Oregon green) platelets. The same sets of experiments are performed with CM-orange labeled CCP-treated chilled platelets transfused into $\alpha M\beta 2$ deficient and WT mice.

In Vivo Anti-Thrombotic Activity of CCP-014.

Initial in vivo experiments administering CCP-014 into both wild-type mice and mice expressing human GPIbα demonstrate that CCP-014 is active in transgenic mice (described in Ware et al., *PNAS* 97:2803-08 (2000)) in which the human GPIbα replaces the mouse platelet GPIbα. CCP-014 extended tail bleeding time, as measured in Ware et al., Id. As expected, CCP-14 is not active in wild-type mice, demonstrating that CCP-014 is specific for the human platelet GPIα. Treatment with CCP-014 demonstrated no overt toxicity at 50 ug per mouse (avg wt=20 gm; dose=approximately 2.5 mg/kg CCP-014.

In Vivo Thrombosis Model [See Hoffmeister et al., US 2008/0138791]

The delivery of room temperature and unmodified chilled platelets to injured endothelium of $\alpha_M\beta 2$ deficient mice can be demonstrated using double fluorescently labeled platelets. The resting blood vessel is monitored for 4 min, then ferric chloride (30l of a 250-mM solution) (Sigma, St Louis, Mo.) is applied on top of the arteriole by superfusion, and video recording resumed for another 10 min. Centerline erythrocyte velocity (Vrbc) is measured before filming and 10 min after ferric chloride injury. The shear rate is calculated on the basis of Poiseuille's law for a Newtonian fluid (Denis, et al, Proc Natl Acad Sci USA 95:9524-29 (1998). These experiments show if chilled platelets have normal hemostatic function. These experiments are repeated in wild-type mice comparing room temperature and CCP-treated chilled murine$^{TG}$ platelets using two different, fluorescently labeled platelet populations injected into the same mouse and analyze thrombus formation and incorporation of both platelet populations.

In vitro platelet functions and survival and in vivo hemostatic activity are measured in untreated chilled and CCP-treated chilled murine$^{TG}$ platelets stored for 1, 5, 7 and 14 days under refrigeration as described above. Recovery and circulation times of these stored untreated chilled and CCP-treated chilled platelets are compared in order to determine that: 1) the modification through CCP-treatment onto chilled murine$^{TG}$ platelets is stable after long-term refrigeration; and 2) the CCP-treated chilled platelets function normally. Survival experiments are performed as described above. As an ultimate test that CCP-treated, stored platelets are functionally intact and contribute to hemostasis, the platelets are transfused into total-body-irradiated mice (Hoyer et al, Oncology 49:166-72 (1992)). To obtain sufficient numbers of platelets, mice are injected with commercially available murine thrombopoietin for seven days to increase their platelet count (Lok et al, Nature 369:565-68 (1994)). Isolated platelets are modified using the optimized CCP-treated protocol, stored under refrigeration, transfused, and tail vein bleeding times measured. Since untreated chilled platelets do not persist in the circulation, a comparison of CCP-treated cooled platelets with room temperature stored platelets is not necessary at this point. The murine$^{TG}$ platelets are stored under refrigeration in standard test tubes. If a comparison with room temperature stored murine$^{TG}$ platelets is desired, primate platelets can be used. Rather than engineer special down-scale, gas-permeable storage containers to accommodate mouse platelets, such comparisons are more appropriate for primates (including humans) for which room temperature storage bags have been designed.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The disclosures of all publications, patents, patent applications and published patent applications referred to herein are hereby incorporated herein by reference in their entirety.

The invention claimed is:

1. A cyclic conjugated peptide (CCP) comprising the amino acid sequence Ala-Cys-Thr-Glu-Arg-Met-Ala-Leu-His-Asn-Leu-Cys-Gly-Gly-Lys, (SEQ ID NO: 4), wherein the C-terminal lysine residue is covalently linked with a polymeric compound and wherein said CCP has the ability to bind in a non-covalent manner to human GPIbα, and said CCP exhibits more potent inhibition of platelet binding to Mac-1 integrin receptors compared to a cyclic peptide comprising the same amino acid sequence, without a covalently linked polymeric compound.

2. The cyclic conjugated peptide of claim 1, wherein the polymeric compound is a polyethylene glycol.

3. The cyclic conjugated peptide of claim 2, wherein the polyethylene glycol has a molecular weight of between 300 and 50,000 daltons.

4. A method for increasing the useful storage life of platelets, said method comprising storing platelets with the cyclic conjugated peptide (CCP) of claim 1; wherein said CCP has the ability to bind in a non-covalent manner to human GPIbα, and said CCP exhibits more potent inhibition of platelet binding to Mac-1 integrin compared to a cyclic peptide comprising the same amino acid sequence, without a covalently linked polymeric compound.

5. The method of claim 4, wherein the platelets are stored at temperatures below 22° C.

6. The method of claim 4, wherein the platelets are stored at temperatures of from about 0° C. to about 4° C.

7. A method of treating a disorder selected from the group consisting of thrombosis, vascular inflammation, and thrombocytopenia, the method comprising administering a CCP of claim 1 to a human subject.

8. A method of claim 7 wherein the CCP is administered in combination with a molecule selected from the group consisting of a VWF antagonist and a TPO mimetic.

9. The method of claim 8, wherein the VWF antagonist is selected from the group consisting of AJW200, ARC-1779, ALX-0081, ALX-0681, GPG-290 or GPIbα-Ig variant fusion polypeptides.

10. The method of claim 8, wherein the TPO mimetic is selected from the group consisting of PROMACTA® (eltrombopag) (GlaxoSmithKline, Inc.) and NPLATE® (romiplostim) (Amgen, Inc.).

11. A cyclic conjugated peptide (CCP) comprising the amino acid sequence Ala-Cys-Thr-Glu-Arg-Met-Ala-Leu-His-Asn-Leu-Cys-Gly-Gly-Lys, (SEQ ID NO: 4), wherein the C-terminal lysine residue is covalently linked with a polymeric compound and wherein said CCP has the ability to bind in a non-covalent manner to GPIbα, and said CCP exhibits more potent inhibition of platelet phagocytosis by cells expressing Ashwell-Morell asialoglycoprotein receptors compared to a cyclic peptide comprising the same amino acid sequence, without a covalently linked polymeric compound.

12. The CCP of claim 11, wherein the polymeric compound is a polyethylene glycol.

13. The CCP of claim 12, wherein the polyethylene glycol has a molecular weight of between 300 and 50,000 daltons.

14. A method for increasing the useful storage life of platelets, said method comprising storing platelets with the cyclic conjugated peptide (CCP) of claim 11; wherein said CCP has the ability to bind in a non-covalent manner to human GPIbα, and said CCP exhibits more potent inhibition of platelet phagocytosis by cells expressing Ashwell-Morell asialoglycoprotein receptors compared to a cyclic peptide comprising the same amino acid sequence, without a covalently linked polymeric compound.

15. The method of claim 14, wherein the platelets are stored at temperatures below 22° C.

16. The method of claim 14, wherein the platelets are stored at temperatures of from about 0° C. to about 4° C.

17. A method of treating a disorder selected from the group consisting of thrombosis, vascular inflammation, and thrombocytopenia, the method comprising administering a CCP of claim 11 to a human subject.

18. A method of claim 17 wherein the CCP is administered in combination with a molecule selected from the group consisting of a VWF antagonist and a TPO mimetic.

19. The method of claim 18, wherein the VWF antagonist is selected from the group consisting of AJW200, ARC-1779, ALX-0081, ALX-0681, GPG-290 or GPIbα-Ig variant fusion polypeptides.

20. The method of claim 18, wherein the TPO mimetic is selected from the group consisting of PROMACTA® (eltrombopag) (GlaxoSmithKline, Inc.) and NPLATE® (romiplostim) (Amgen, Inc.).

\* \* \* \* \*

SEQUENCE LISTING

<160> NUMBER OF SEQ ID NOS: 9

<210> SEQ ID NO 1
<211> LENGTH: 15
<212> TYPE: PRT
<213> ORGANISM: Artificial Sequence
<220> FEATURE:
<223> OTHER INFORMATION: Artificial - synthesized in laboratory

<400> SEQUENCE: 1

Ala Cys Thr Glu Arg Met Ala Leu His Asn Leu Cys Gly Gly Lys
1               5                   10                  15

```
<210> SEQ ID NO 2
<211> LENGTH: 15
<212> TYPE: PRT
<213> ORGANISM: Artificial Sequence
<220> FEATURE:
<223> OTHER INFORMATION: Synthesized in lab

<400> SEQUENCE: 2

Ala Cys Thr Glu Arg Met Ala Leu His Asn Leu Cys Gly Gly Lys
1               5                   10                  15

<210> SEQ ID NO 3
<211> LENGTH: 22
<212> TYPE: PRT
<213> ORGANISM: Artificial Sequence
<220> FEATURE:
<223> OTHER INFORMATION: Synthesized in lab
<220> FEATURE:
<221> NAME/KEY: MISC_FEATURE
<222> LOCATION: (5)..(5)
<223> OTHER INFORMATION: Xaa is Met, Asp, Leu, Trp or Ala
<220> FEATURE:
<221> NAME/KEY: MISC_FEATURE
<222> LOCATION: (12)..(20)
<223> OTHER INFORMATION: Each Xaa is absent or any amino acid except C
<220> FEATURE:
<221> NAME/KEY: MISC_FEATURE
<222> LOCATION: (21)..(21)
<223> OTHER INFORMATION: Xaa is any amino acid except C
<220> FEATURE:
<221> NAME/KEY: MISC_FEATURE
<222> LOCATION: (22)..(22)
<223> OTHER INFORMATION: K is optionally pegylated

<400> SEQUENCE: 3

Cys Thr Glu Arg Xaa Ala Leu His Asn Leu Cys Xaa Xaa Xaa Xaa Xaa
1               5                   10                  15

Xaa Xaa Xaa Xaa Xaa Lys
            20

<210> SEQ ID NO 4
<211> LENGTH: 32
<212> TYPE: PRT
<213> ORGANISM: Artificial Sequence
<220> FEATURE:
<223> OTHER INFORMATION: Synthesized in laboratory
<220> FEATURE:
<221> NAME/KEY: MISC_FEATURE
<222> LOCATION: (1)..(1)
<223> OTHER INFORMATION: Xaa is any amino acid except C; and is
      optionally pegylated
<220> FEATURE:
<221> NAME/KEY: MISC_FEATURE
<222> LOCATION: (2)..(10)
<223> OTHER INFORMATION: Each Xaa is absent or any amino acid except C;
<220> FEATURE:
<221> NAME/KEY: MISC_FEATURE
<222> LOCATION: (15)..(15)
<223> OTHER INFORMATION: Xaa is Met, Asp, Leu, Trp or Ala
<220> FEATURE:
<221> NAME/KEY: MISC_FEATURE
<222> LOCATION: (22)..(31)
<223> OTHER INFORMATION: Each Xaa is absent or any amino acid except C;
<220> FEATURE:
<221> NAME/KEY: MISC_FEATURE
<222> LOCATION: (32)..(32)
<223> OTHER INFORMATION: K is optionally pegylated

<400> SEQUENCE: 4

Xaa Xaa Xaa Xaa Xaa Xaa Xaa Xaa Xaa Xaa Cys Thr Glu Arg Xaa Ala
1               5                   10                  15

Leu His Asn Leu Cys Xaa Xaa Xaa Xaa Xaa Xaa Xaa Xaa Xaa Xaa Lys
```

<210> SEQ ID NO 5
<211> LENGTH: 31
<212> TYPE: PRT
<213> ORGANISM: Artificial Sequence
<220> FEATURE:
<223> OTHER INFORMATION: Synthesized in lab
<220> FEATURE:
<221> NAME/KEY: MISC_FEATURE
<222> LOCATION: (1)..(1)
<223> OTHER INFORMATION: Xaa is any amino acid except C; and is
      optionally pegylated
<220> FEATURE:
<221> NAME/KEY: MISC_FEATURE
<222> LOCATION: (2)..(10)
<223> OTHER INFORMATION: Each Xaa is absent or any amino acid except C;
<220> FEATURE:
<221> NAME/KEY: MISC_FEATURE
<222> LOCATION: (15)..(15)
<223> OTHER INFORMATION: Xaa is Met, Asp, Leu, Trp or Ala
<220> FEATURE:
<221> NAME/KEY: MISC_FEATURE
<222> LOCATION: (22)..(30)
<223> OTHER INFORMATION: Each Xaa is absent or any amino acid except C;
<220> FEATURE:
<221> NAME/KEY: MISC_FEATURE
<222> LOCATION: (31)..(31)
<223> OTHER INFORMATION: Xaa is any amino acid except C;

<400> SEQUENCE: 5

Xaa Xaa Xaa Xaa Xaa Xaa Xaa Xaa Xaa Xaa Cys Thr Glu Arg Xaa Ala
1               5                   10                  15

Leu His Asn Leu Cys Xaa Xaa Xaa Xaa Xaa Xaa Xaa Xaa Xaa Xaa
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Synthesized in lab
<220> FEATURE:
<221> NAME/KEY: MISC_FEATURE
<222> LOCATION: (1)..(1)
<223> OTHER INFORMATION: Xaa is any amino acid except C, and is
      optionally pegylated
<220> FEATURE:
<221> NAME/KEY: MISC_FEATURE
<222> LOCATION: (2)..(10)
<223> OTHER INFORMATION: Each Xaa is absent or any amino acid except C
<220> FEATURE:
<221> NAME/KEY: MISC_FEATURE
<222> LOCATION: (15)..(15)
<223> OTHER INFORMATION: Xaa is Met, Asp, Leu, Trp or Ala
<220> FEATURE:
<221> NAME/KEY: MISC_FEATURE
<222> LOCATION: (22)..(30)
<223> OTHER INFORMATION: Each Xaa is absent, or any amino acid except
      Cys
<220> FEATURE:
<221> NAME/KEY: MISC_FEATURE
<222> LOCATION: (31)..(31)
<223> OTHER INFORMATION: Xaa is any amino acid except Cys, and is
      optionally pegylated

<400> SEQUENCE: 6

Xaa Xaa Xaa Xaa Xaa Xaa Xaa Xaa Xaa Xaa Cys Thr Glu Arg Xaa Ala
1               5                   10                  15

Leu His Asn Leu Cys Xaa Xaa Xaa Xaa Xaa Xaa Xaa Xaa Xaa Xaa
            20                  25                  30

```
<210> SEQ ID NO 7
<211> LENGTH: 15
<212> TYPE: PRT
<213> ORGANISM: Artificial Sequence
<220> FEATURE:
<223> OTHER INFORMATION: Synthesized in lab
<220> FEATURE:
<221> NAME/KEY: MISC_FEATURE
<222> LOCATION: (15)..(15)
<223> OTHER INFORMATION: G is optionally pegylated

<400> SEQUENCE: 7

Ala Cys Thr Glu Arg Met Ala Leu His Asn Leu Cys Gly Gly Gly
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthesized in lab
<220> FEATURE:
<221> NAME/KEY: MISC_FEATURE
<222> LOCATION: (1)..(1)
<223> OTHER INFORMATION: G is optionally pegylated

<400> SEQUENCE: 8

Gly Cys Thr Glu Arg Asp Ala Leu His Asn Leu Cys Gly Gly Gly Gly
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthesized in lab
<220> FEATURE:
<221> NAME/KEY: MISC_FEATURE
<222> LOCATION: (1)..(1)
<223> OTHER INFORMATION: A is optionally pegylated
<220> FEATURE:
<221> NAME/KEY: MISC_FEATURE
<222> LOCATION: (15)..(15)
<223> OTHER INFORMATION: G is optionally pegylated

<400> SEQUENCE: 9

Ala Cys Thr Glu Arg Met Ala Leu His Asn Leu Cys Ser Ser Gly
1               5                   10                  15
```